United States Patent [19]
Gillum

[11] Patent Number: 5,573,730
[45] Date of Patent: Nov. 12, 1996

[54] METHOD AND APPARATUS FOR TREATING AIRBORNE RESIDUES

[76] Inventor: Theodore J. Gillum, 10 Forest Rd., Budd Lake, N.J. 07828

[21] Appl. No.: 438,008

[22] Filed: May 9, 1995

[51] Int. Cl.⁶ .................................................. A62B 7/08
[52] U.S. Cl. .................. 422/123; 422/110; 422/111; 422/120; 422/121; 422/124; 422/186.07; 422/186.14
[58] Field of Search .................... 422/4, 5, 120, 422/121, 123, 124, 105, 108, 110, 111, 186.07, 186.14, 186.15

[56] References Cited

U.S. PATENT DOCUMENTS

| | | | |
|---|---|---|---|
| 3,070,976 | 1/1963 | Guhl | 422/124 X |
| 3,745,750 | 7/1973 | Arff | 422/121 X |
| 4,035,301 | 7/1977 | Armstrong | 210/220 |
| 4,204,955 | 5/1980 | Armstrong | 210/61 |
| 4,572,821 | 2/1986 | Brodard et al. | 422/186.12 |
| 4,640,782 | 2/1987 | Burleson | 210/748 |
| 4,904,289 | 2/1990 | Miyakami et al. | 422/121 X |
| 5,063,030 | 11/1991 | Sweetman | 422/189 |
| 5,123,176 | 6/1992 | Yamada et al. | 34/32 |
| 5,151,197 | 9/1992 | Smith et al. | 210/758 |
| 5,173,268 | 12/1992 | Weaver | 422/121 |
| 5,205,927 | 4/1993 | Wickramanayake | 210/170 |

*Primary Examiner*—Robert J. Warden
*Assistant Examiner*—Krisanne M. Thornton
*Attorney, Agent, or Firm*—Morgan & Finnegan, L.L.P.

[57] ABSTRACT

An ozone generator is disclosed in which ozone production is controlled through corona voltage and airflow. The ozone from the generator converts perchloroethylene vapor in dry cleaning effluents into environmentally acceptable compounds. Ozone generation is controlled in response to the perchloroethylene vapor concentration in the mixture that is discharged from a mixing chamber in the apparatus. Other features include an inflatable retention chamber for allowing the ozone and perchloroethylene reaction to go to completion and improved means for cleaning the glass plates in the ozone generator by sliding the plates out of the generator structure.

6 Claims, 7 Drawing Sheets

METHOD AND APPARATUS FOR TREATING AIRBORNE RESIDUES

BACKGROUND OF THE INVENTION

1. Field of the Invention

This invention relates to methods and apparatus for treating airborne residues and, more particularly, to a safe application of ozone to the airborne perchloroethylene vapor that is emitted from dry cleaning processes in order to convert the vapor into harmless substances for release to the atmosphere, and the like.

2. Description of the Prior Art

There is a need to protect the atmosphere from degradation in quality through contaminants that are released in the course of any number of industrial processes. Illustratively, with increasing population and a matching growth in industrial activity, the discharge into the atmosphere of contaminants which are attributable to these sources is swiftly reaching and, in some cases, may already have exceeded the earth's natural capacity to absorb pollutants of this nature. As a consequence, many industries are taking measures to reduce the burden that their products and processes had heretofore imposed on the environment. Environmental protection laws have also been enacted not only to encourage those industries that have thus far failed to adopt environmental protection programs to nevertheless take necessary action, but also to establish some tangible standards for acceptable emission levels.

Typical of these industrial processes is the process for dry cleaning clothing in which the garments that are to be cleansed are treated with perchloroethylene, a volatile organic solvent. After cleansing with perchloroethylene, and largely as a matter of process economics, most of the perchloroethylene solvent and vapor is recovered to be used again. These perchloroethylene recovery techniques, however, reclaim only about 98% of the solvent and vapor. The remaining 2% of the solvent is often released to the atmosphere as an un-recoverable vapor. Clearly, there is a need for an efficient and economical system that can treat most, if not all, of the otherwise escaping perchloroethylene vapor in order to prevent this vapor from becoming an environmental contaminant.

A number of proposals for suitably treating potentially harmful industrial compounds that otherwise would discharge into the environment have been advanced through the years. Typical of these proposals are:

U.S. Pat. No. 5,205,927 granted Apr. 27, 1993 to G. B. Wickramanayake for "Apparatus For Treatment of Soils Contaminated With Organic Pollutants" which discloses an apparatus for generating ozone, that is, an unstable oxygen molecule of three oxygen atoms, $O_3$, in contrast to the usual, stable two oxygen atom ($O_2$) molecule. It should be noted, in this respect, that extremely small quantities of ozone occur in the atmosphere through normal environmental processes. This patent describes generating artificially produced ozone, however, in a gas that is applied to contaminated soil in order to decompose the contaminating organic compounds that are in the soil.

U.S. Pat. No. 5,151,197 granted Sep. 29, 1992 to A. J. Smith et al. for "Fluid Treatment" shows an apparatus for treating liquid wastes with oxygen, oxygen enhanced air or ozonated air.

U.S. Pat. No. 5,123,176 granted Jun. 23, 1992 to K. Yamada et al. for "Method And Apparatus For Dry Cleaning As Well As Method And Device For Recovery Of Solvent Therein" is directed to a dry cleaning device in which the solvent gas is reused.

U.S. Pat. No. 4,640,782 granted Feb. 3, 1987 to J. C. Burleson for "Method And Apparatus For The Generation And Utilization Of Ozone And Singlet Oxygen" discloses an apparatus for generating ozone and singlet, or "nascent" oxygen ($O_1$). Nascent oxygen is composed of single oxygen atoms, unattached to any other substance. Oxygen in this form is highly unstable and swiftly combines, usually with another oxygen atom, to form a stable $O_2$ molecule. The ozone and nascent oxygen are, as stated in this patent, mixed with pathogens to kill the pathogens.

U.S. Pat. No. 4,572,821 granted Feb. 25, 1986 to E. Brodard et al. for "Apparatus For Dissolving Ozone In A Fluid" shows a device for mixing an ozonized gas with a fluid and from which a mixture of fluid and ozonized gas is discharged.

U.S. Pat. No. 4,204,955 granted May 27, 1980 to E. T. Armstrong for "System For Pollution Suppression" is directed to an apparatus for increasing the ozone concentration in a gas and mixing the gas with fluid waste.

U.S. Pat. No. 4,035,301 granted Jul. 12, 1977 to E. T. Armstrong for "System For Pollution Suppression" shows a surge suppression apparatus and a gas purifying scrubber.

Although several of these foregoing proposals suggest the use of ozone to convert organic matter into environmentally compatible compounds, none of these proposals suggest a way in which ozone can be produced and applied with safety, efficiency and economy to an organic vapor in order to reach this result.

In this respect, as noted above, oxygen, in its usual, stable state occurs generally in a molecule of two oxygen atoms. Through appropriate treatment, e.g., application of a high voltage electrical field to a supply of oxygen, or some other oxygen bearing gas, limited quantities of ozone molecules are produced.

With specific emphasis on perchloroethylene vapor treatment, ozone combines through a sequence of chemical reactions with the perchloroethylene to produce carbon dioxide ($CO_2$), water ($H_2O$), more oxygen ($O_2$) and some simple chloride compounds. All of these reaction products are environmentally acceptable. Further in this respect, although the additional oxygen ($O_2$) creates a somewhat fresher atmosphere and the air quality also is improved because airborne bacteria, odors and the like are destroyed, nevertheless great care must be exercised in connection with the ozone that is generated.

For example, prolonged or continued exposure to ozone in concentrations of 0.10 parts per million (ppm) is toxic. Because, as mentioned above, very small concentrations of ozone occur naturally in the atmosphere, humans and animals do have a tolerance, or acceptance level for this gas. Thus, it has been learned that concentrations of ozone of 0.05 ppm or less have no toxic effect on human beings or on animals. Because the ozone molecule is so unstable, it also has been learned that these molecules will separate in not more than about thirty minutes after formation into the usual, stable oxygen molecule of two oxygen atoms ($O_2$), the third oxygen atom from the ozone molecule linking up with any other molecule that can accept it.

Prior art ozone generators also were subject to a rapid accumulation of oxidized particles on the plate or tubular ozone generator surfaces to an extent that generator operation between maintenance cleanings was reduced to a few dozen hours. To make matters even more difficult, unbolting and removing these plate or tubular generator surfaces for cleaning was a tedious and time-consuming business, requiring the fouled generator tubes or plates to be withdrawn individually from the ozone generator. This, of course, aggravated the short operational span that characterized these generators by imposing lengthy maintenance periods.

These ozone generators were also subject to a number of additional disadvantages. For instance, there is the problem of isolating the ozone generator from potentially explosive vapors. There is the further problem of ozone generation efficiency. Prior art ozone generators, for example, used high volume air bypass apparatus for ozone production. More than 95% of the process air in these bypass systems did not come into contact with the electrical fields that produced the ozone, but flowed over the outside of the plates or tubes that were used to establish these electrical fields. This produced a very low conversion rate (less than 1/100 of one percent of the available oxygen molecules were converted into ozone molecules) and the requirement for large, inefficient and bulky apparatus with high volume air handling capacities to generate the needed ozone concentration. These prior art ozone generators were also unsatisfactory because the air handling and ozone generation capacity for each device was inflexibly fixed. In this circumstance, a different size ozone generator was required to meet each separate commercial air handling and ozone production requirement.

Accordingly, there is a need for a safer and more efficient and economical apparatus for generating and applying ozone to various substances in order to convert these substances, of which perchloroethylene is typical, into environmentally acceptable compounds. More specifically, there is a need for an improved ozone generator that has greater conversion efficiency with a lower volume of process air. There is, moreover, a further need for an ozone generator that is readily adaptable to different air handling and ozone concentration requirements.

SUMMARY OF THE INVENTION

These and other deficiencies that have characterized the prior art are overcome, to a great extent, through the practice of the invention. Illustratively, a typical ozone generator in accordance with the principles of the invention, eliminates the air bypass feature that characterized the prior art and exposes at least 95% of the available oxygen molecules flowing through the generator to an electrical field, thereby increasing the oxygen to ozone conversion rate by a factor of 250. Thus, an apparatus that characterizes the invention not only improves the oxygen to ozone conversion rate, but also enables this conversion to be achieved with considerably less process air. In this way, process efficiency is increased with a smaller generator through a much better conversion rate and significantly lower air handling requirements.

A unique feature of the ozone generator is its adaptability to different ozone conversion demands within a broad range of process air flows, or throughputs. By selectively adding or removing some of the plates that establish the ozone generator's electrical field, ozone production can be varied to produce a desired concentration. In this way, the invention separates ozone generation efficiency from process air flow, thereby providing two variables that can be manipulated to produce a range of air flow rates and ozone concentrations from a single generator, in contrast to the rigidly inflexible output characteristics that were so typical of prior art ozone generators.

Further in this regard, by mounting the plates on which the oxidized particles accumulate in a manner that enables these plates to be swiftly withdrawn from the ozone generator for cleaning, a significant reduction is provided in the time that heretofore had been required to remove and clean fouled plates in prior art devices.

As a part of the overall system that characterizes the invention for converting potential atmospheric pollutants into environmentally harmless substances, the system is attached, in the illustrative case of perchloroethylene vapor emitted from a dry cleaning machine, directly to the dry cleaning machine's air recirculation system. With respect to this embodiment of the invention, the oxidation chamber, in which the ozone is mixed with the perchloroethylene vapor, is connected in fluid communication with the machine's cleaning drum. This arrangement generally isolates the ozone injection system for safety purposes and permits higher and more efficient concentrations of ozone to be applied to the solvent vapor.

In this manner, all of the air is exhausted from the dry cleaning machine through the oxidation chamber. This treated air with ozone enrichment then is reintroduced into the dry cleaning process.

To match ozone production to perchloroethylene neutralization requirements, an airborne vapor sensor responds to the oxidation chamber discharge by sending a signal to a microprocessor that regulates the ozone generator output. In this manner, a correspondence between perchloroethylene vapor load and ozone production is maintained.

Also, depending on the vapor that is being treated, a portion of the treated vapor can be vented to the atmosphere to prevent over pressurization in the oxidation chamber, and as circumstances may dictate, a secondary retention chamber can be provided to hold the treated vapor for a sufficient time to allow the oxidation reaction to proceed to an essential completion before discharge into the atmosphere. A further aspect of the invention is the use of inflatable retention chambers for this purpose. The discharge ventilation fan, or blower, inflates these retention chambers which can be installed in locations that are unsuited to rigid chambers.

When vented to the atmosphere, the excess ozone in the discharged gas dissipates rapidly because of the unstable nature of the ozone molecule. For safety purposes, however, the ozone concentration level is calculated and the dry cleaning machine operating set points are developed on the conservative assumption that no oxidation occurs in the treated airstream. Under ideal conditions, 99.5% of the available ozone will react with perchloroethylene, the remaining trace quantities of ozone dissipating, under ordinary conditions of atmospheric pressure and temperature, in not more than thirty minutes.

Thus, there is provided in accordance with the invention an improved ozone generator and system for converting potentially hazardous vapors into environmentally acceptable compositions. These features of the invention are described more specifically in connection with the following detailed description of a preferred embodiment of the invention, taken with the figures of the drawing. The scope of the invention, however, is limited only through the claims appended hereto.

DESCRIPTION OF THE PREFERRED EMBODIMENT

Figure 1:
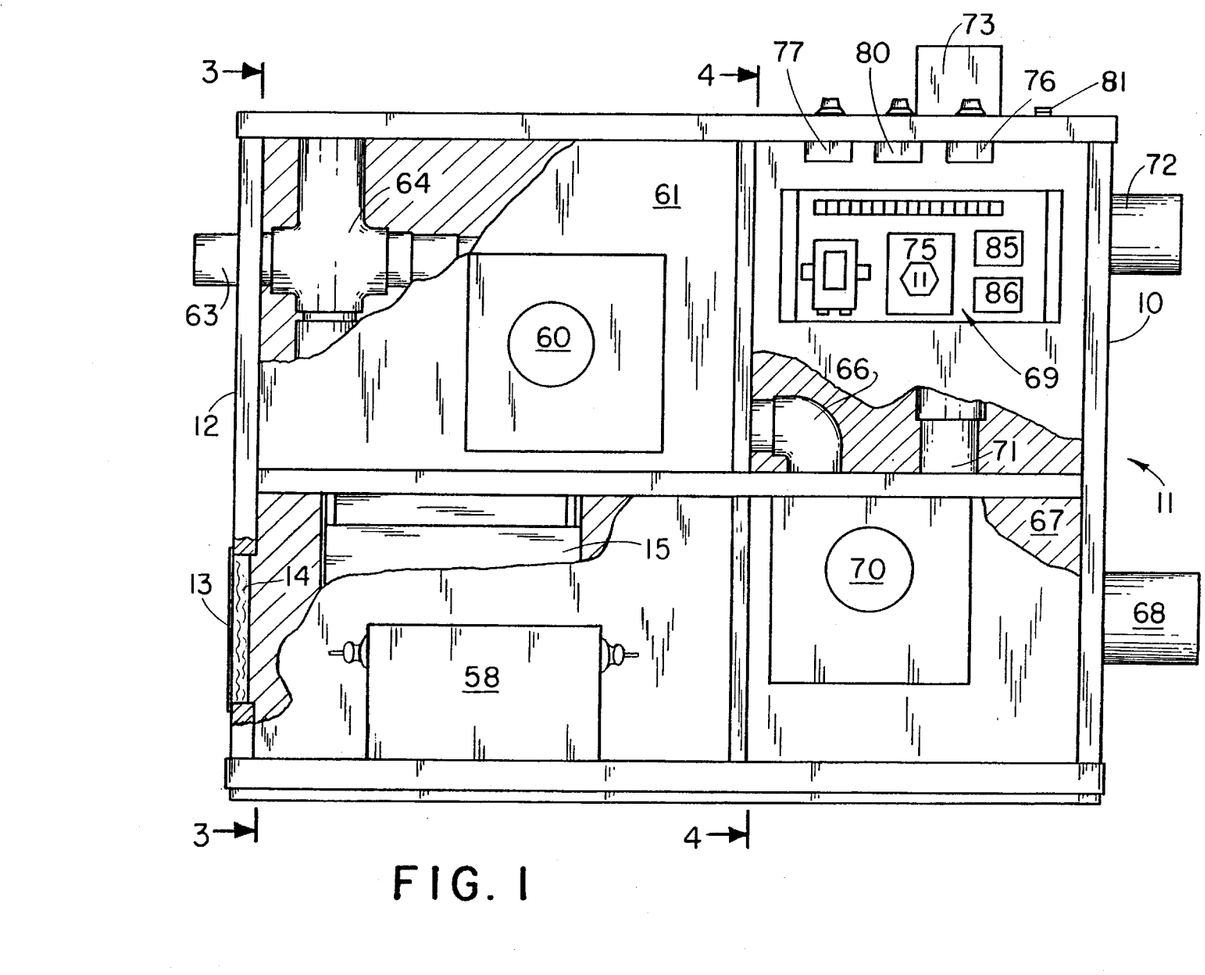
FIG. 1 is a front view of a typical embodiment of the invention, from which the front panel has been removed and portions of interior partitions broken away to better illustrate the internal structure of the apparatus.

For a more complete appreciation of the invention, attention is invited to FIG. 1 which shows a housing 10 for a vapor or perchloroethylene treatment apparatus 11. As illustrated, and in accordance with the principles of the invention described subsequently in greater detail, the housing 10 occupies a relatively small floorspace of about 4.75 square feet. A side cover 12, which forms a part of the housing 10, has a generally rectangular air inlet 13 formed in its lower portion. A replaceable air filter 14 is inserted in the air inlet 13 to remove particulate matter from air that is drawn from the surrounding atmosphere for use in the apparatus 11.

Figure 3:
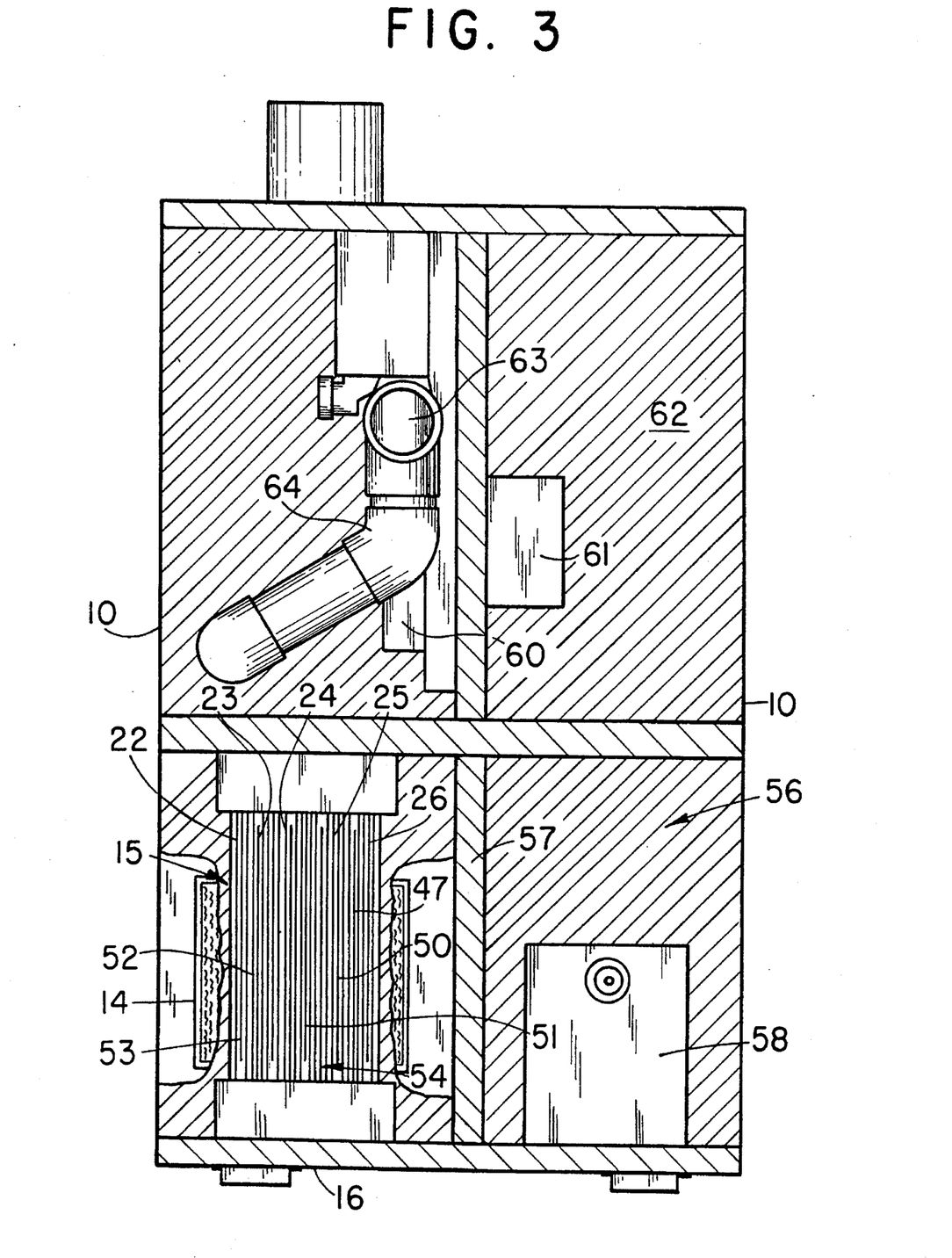
FIG. 3 is a side view of the apparatus, in full section, taken along the line 3—3 of FIG. 1 and viewed in the direction of the arrows.
Figure 6:
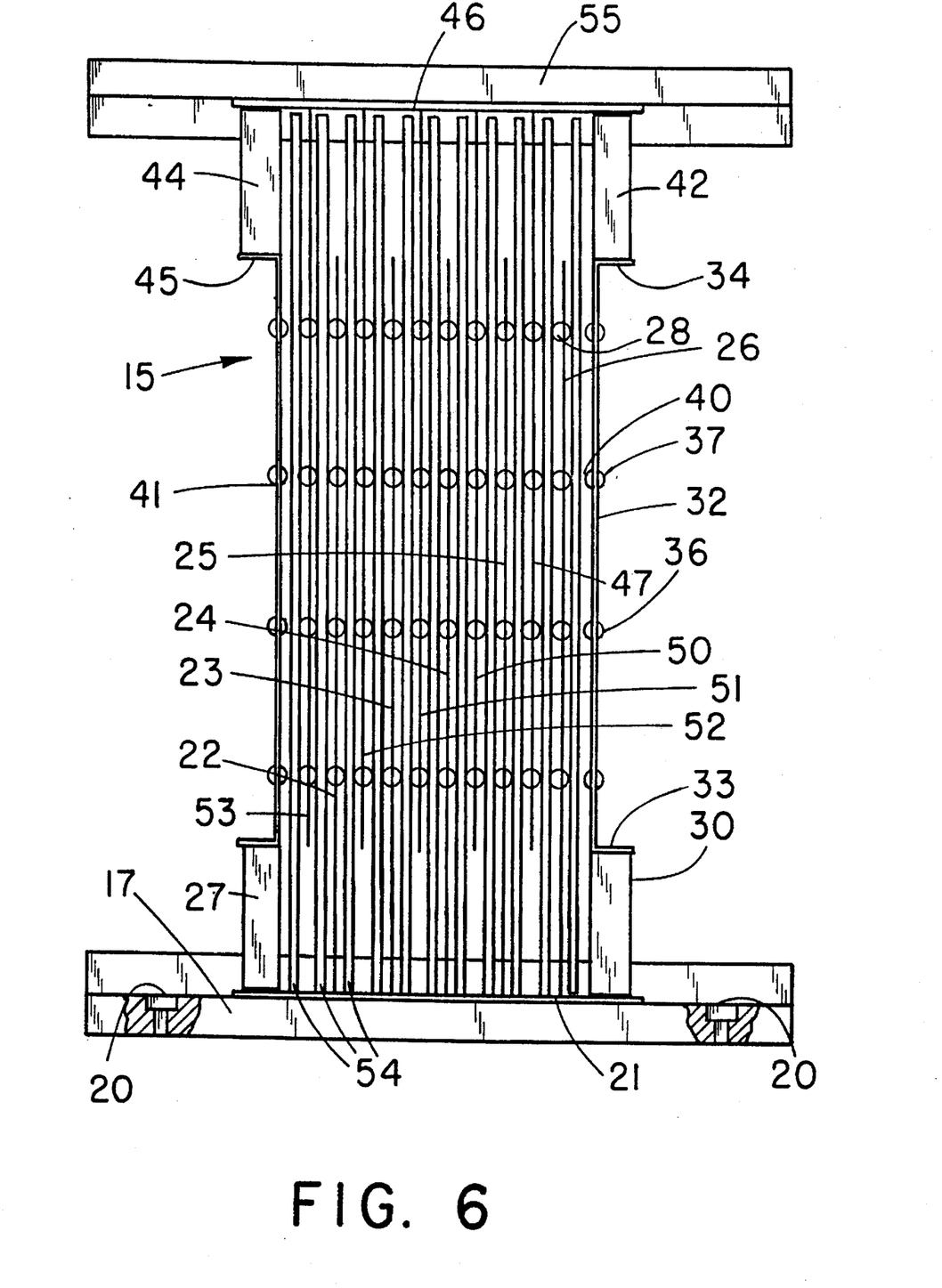
FIG. 6 is a front view of the ozone generator taken along the line 6—6 of FIG. 5 and viewed in the direction of the arrows.

The filter 14 is in alignment with the front of an ozone generator 15. As best shown in FIG. 3, the ozone generator 15 is mounted on a base 16 of the housing 10. Turning now to FIG. 6, the illustrative ozone generator 15 is generally rectangular in shape, and is about 9½ inches wide by 13 inches high and has an overall length of 11½ inches. A sheet 17 of phenolic resin or other suitable electrical insulating material has a set of four countersunk bolt holes 20 to attach the ozone generator 15 to the base 16 (FIG. 3) of the housing 10. The sheet 17 ( FIG. 6), moreover, electrically insulates the ozone generator from the housing. Centered on the plate 17 is a generally rectangular, horizontally disposed electrical conductor 21 to which are mounted, in electrical contact, a first set of five rectangular and longitudinally positioned vertical plates 22, 23, 24, 25 and 26. The vertical plates 22 through 26 are positioned, relative to the insulating plate 17 in a direction that orients the vertical edges of these plates in the direction of the air filter 14, shown in FIG. 1. Further, the plates each have four vertically spaced rows of dimples 28, aligned horizontally in each respective row. These dimples 28 protrude alternately from the flat opposite sides of each of these electrically conducting plates. Preferably, the dimples 28 each have a diameter of about 0.280 inches and a depth of about 0.125 inches. Thus, as air is drawn into the housing 10 (FIG. 3), it is these vertical edges of the plates 22 through 26 (FIG. 6) that divide essentially all of the incoming air to pass across breadth of both sides of each plate.

Figure 5:
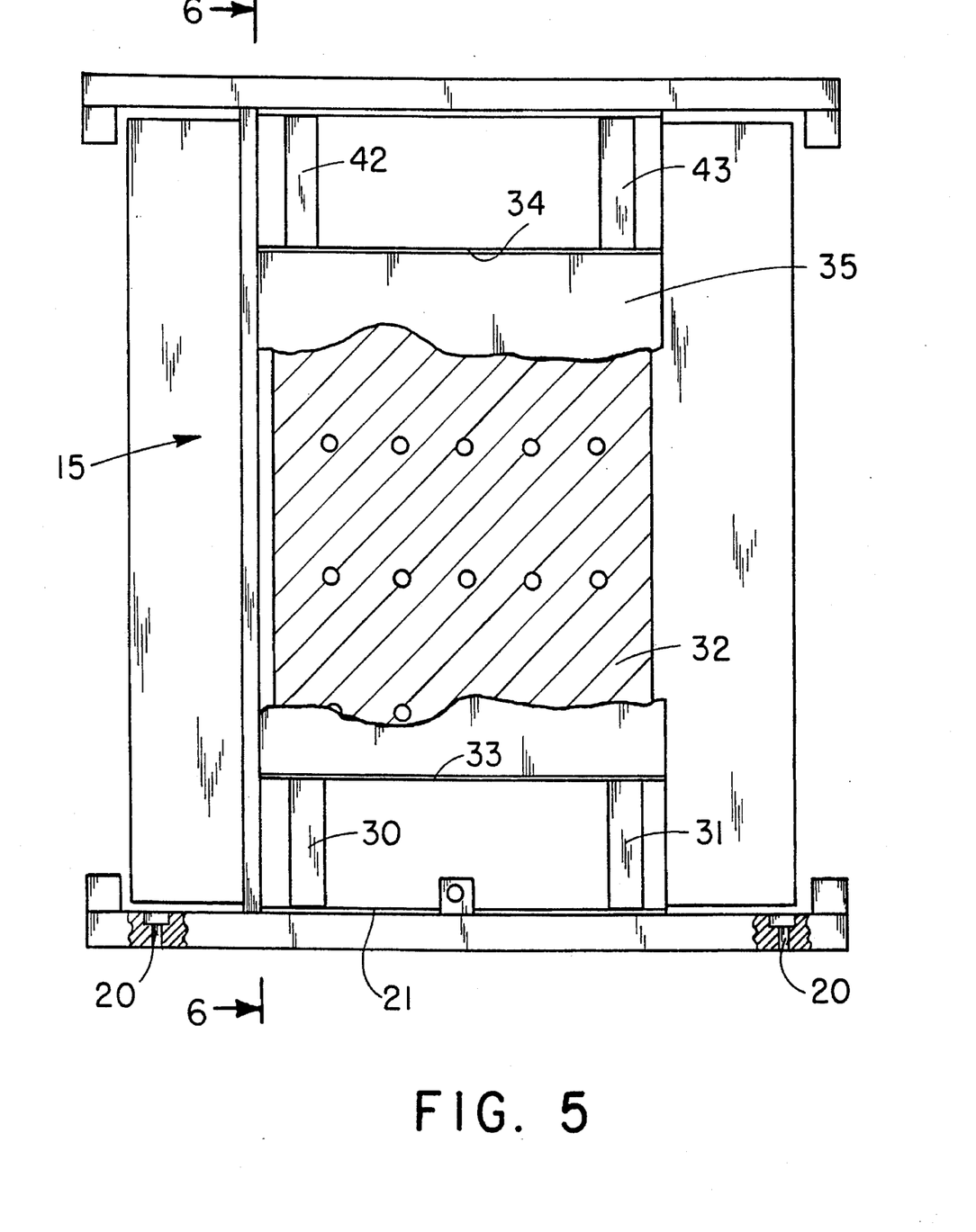
FIG. 5 is a side view of an ozone generator suitable for use in the apparatus shown in FIGS. 1 through 4 in which portions of the stabilizer are broken away to better illustrate the generator's internal construction.

Turning once more to the ozone generator 15, it should be noted that there are a set of four vertical electrical insulators, of which only insulators 27, 30 and 31 are shown in FIGS. 5 and 6. Each of these resistors is mounted in a respective one of the four corners of the electrically conducting plate 21. The insulators 30, 31 support a shallow, channel shaped stabilizer 32. Preferably, the stabilizer 32 is formed from 0.016 inch type 304 stainless steel in which the plate 32 has a lower, horizontally protruding flange 33 and an upper, horizontally protruding flange 34. The vertical portion of the stabilizer 32, however, is a generally flat sheet 35 in which four horizontal rows of dimples 36 have been formed. These dimples, moreover, have dimensions that are essentially the same as those described with respect to the electrically conducting plates 22 through 26. The stabilizer dimples 36 alternate in their respective horizontal orientations, an illustrative dimple 37 protruding away from the first electrically conducting plate 26 and the next dimple 40 in that row protruding inwardly, toward the first electrically conducting plate 26.

A similarly constructed, electrically insulated and dimpled stabilizer 41 is provided on the opposite side of the ozone generator 15, near the first electrically conducting plate 22.

The flange 34 supports, at its respective longitudinal ends a further pair of electrical insulators 42, 43 (FIG. 5). An equivalent pair of vertical insulators, of which only the insulator 44 is shown in FIG. 6, also are mounted on upper flange 45 of the stabilizer 41. These four insulators, of which only the insulators 42, 43 and 44 are shown in the drawing, provide electrical insulation and structural support for a horizontally disposed generally rectangular electrical conductor 46 that essentially matches the size and shape of the electrical conductor 21, as well as overlaying that conductor.

A second set of five electrically conducting, dimpled plates 47, 50, 51, 52, 53 that correspond generally in size and shape to the first electrically conducting plates 22 through 27, are in electrical contact with and depend vertically from the electrical conductor 46. Apart from the outermost plates 26 and 53, the plates 22 through 26 are interleaved between and spaced from the corresponding plates 47 and 50 through 52. The sizes of both the first and second sets of electrically conducting plates, however, are such that they overlay each other only in the vertical portion of the ozone generator 15 in the volume that is delineated between the sets of vertical insulators 27, 30, 31 and 42, 43 and 44.

Individual sheets 54 of ⅛ inch thick tempered glass are each sandwiched, or interposed between each of the respective adjacent electrically conducting plates in the first and second sets of these plates. The glass sheets 54, moreover, each are spaced from the adjoining pair of the electrically conductive plates in the first and second sets by means of the rows of dimples 36 which protrude from the conductive plates and bear against these adjoining glass sheets that sandwich the respective plates. Further in this regard, the glass 54 also extend through the entire height of the space between the horizontally disposed electrical conductors 21 and 46.

In accordance with a feature of the invention, each of the glass plates 54 can be removed from its respective position within the ozone generator 15 by drawing the plate from the generator in a direction parallel to the orientation of the first and second sets of electrically conductive plates, the bottoms of the plates bearing against and sliding on the electrical conductor 21. This construction simplifies the task of removing the glass plates 54 from the ozone generator 15 to cleanse the plates of oxide residues. To restore the glass plates 54, it is only necessary to push them back into the generator 15, the bottoms of the glass plates each sliding on a portion of the electrical conductor 21.

Further in this regard, with the glass plates 54 in their nested position, it can be seen that the sets of dimples 28, 37 and 40, lend structural stability and rigidity to the ozone generator 15 as these dimples bear against their adjoining glass plates 54.

The electrical conductor 46 is secured to a horizontal insulating member 55 of phenolic resin or other suitable insulating material.

Turning to FIG. 3, the ozone generator 15 is separated from a high voltage compartment 56 by a partition 57 that isolates the ozone generator 15 from a high voltage power supply 58. A typical high voltage power supply, suitable for use in connection with the invention is a Franceformer 15030p.0–15,000 volt supply.

Air is drawn through the filter 14 (FIG. 1) and through the ozone generator 15 under a draft from radial wheel ozone delivery blower 60 that has a capacity which can be varied in flow rate from zero to fifty cubic feet of air per minute. A Kooltronic Model KBR-75 with S/S wheel and an epoxy coated blower housing is suitable for this application. The fan portion of the blower 60 is mounted in a compartment that is in fluid communication with the ozone generator 15. The blower 60 has a motor 61, however, that is mounted in a separate, blower motor compartment 62. For safety purposes, the motor compartment is sealed and coated with corrosion resistant polymers in order to isolate the blower and the ozone stream from the balance of the components.

Figure 2:
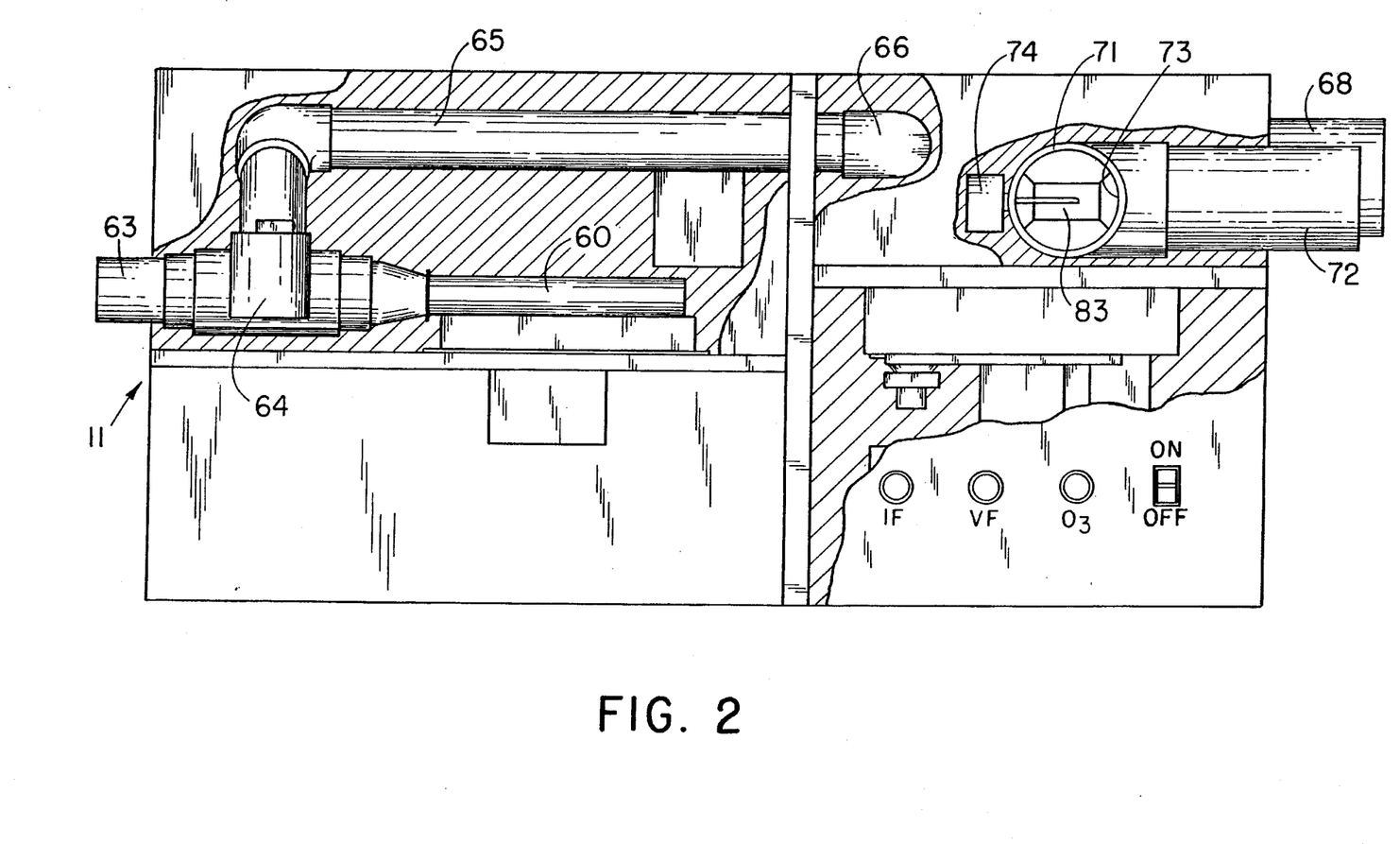
FIG. 2 is a top view of the apparatus shown in FIG. 1 from which a portion of the top cover has been removed.
Figure 4:
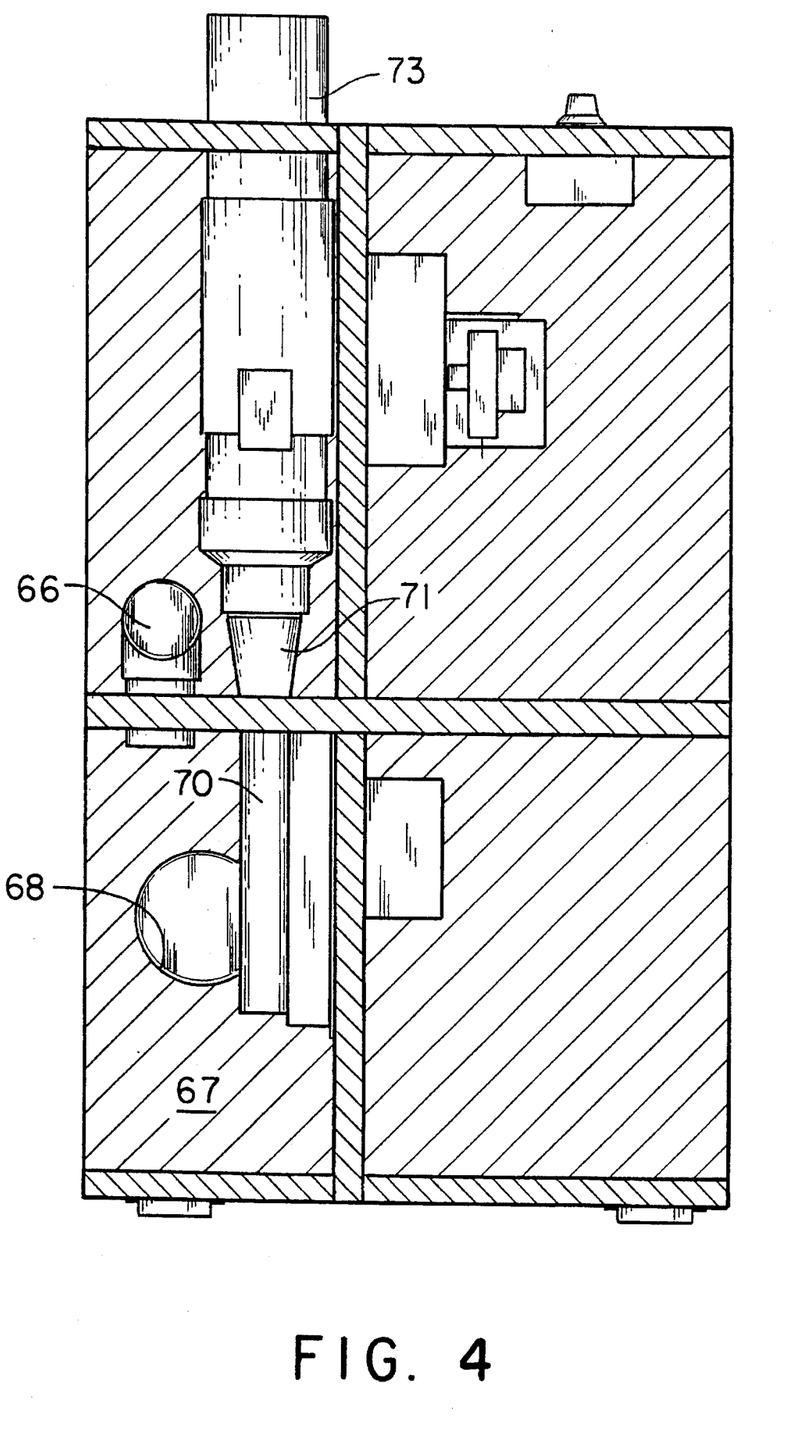
FIG. 4 is a side view of the apparatus, in full section, taken along the lines 4—4 of FIG. 1 and viewed in the direction of the arrows.

As shown in FIGS. 1 and 3, the ozone delivery blower 60 communicates directly with a direct ozone discharge outlet 63 through an automatic diverting valve 64 (FIG. 2). Ozone discharge through the outlet 63 is used if direct treatment with ozone of a volume (not shown) is required. The automatic diverting valve 64 also selectively allows ozonated air from the blower 60 to discharge directly through a conduit 65 that includes an ell 66 (FIGS. 1, 2 and 4). The ell 66 directs diverted ozonated air from the blower 60 downwardly into an ozone-airborne vapor mixing compartment 67 that is best illustrated in FIG. 4. This mixing compartment 67 is the reaction volume in which the ozone reacts with most of the perchloroethylene vapor to reduce this vapor to environmentally acceptable oxygen molecules ($O_2$); water; carbon dioxide and simple chlorides. A selectively operated odor pick up inlet 68 that is in fluid communication with the mixing compartment 67 also is provided to establish a connecting point for coupling flexible ducting from the mixing compartment 67 to the odor source (not shown).

The ozone, remaining perchloroethylene vapor and reaction products can be discharged from the mixing compartment 67 in two directions. Thus, a zero to fifty cubic feet per minute vent blower 70 (FIG. 4), of the same type as that which was described in connection with the blower 60, not only draws odors into the mixing compartment 67 through the inlet 68, but also draws the gaseous mixture from the mixing compartment 67 and passes this mixture up through vent diverter piping 71 for discharge either through a treated odor recirculation outlet 72 (FIGS. 1 and 2) or through a treated odor vent outlet 73.

The disposition of the gaseous mixture, either for recirculation from the outlet 72 or for complete discharge to the atmosphere from the outlet 73 is controlled by means of a perchloroethylene sensor probe 74 (FIG. 2). A typical perchloroethylene sensor probe suitable for use with the invention is a G-Controls Model SDQ-010, VOC sensor, which can detect chlorine bearing compounds to a resolution of 1 part per million (ppm) and generate a variable output signal in the range of 0 to 10 volts direct current. Thus, depending on the sensed perchloroethylene concentration, the treated mixture can be discharged through the recirculation outlet 72 in order to recycle the gas within a closed loop process system. The treated gas, however, also can be discharged through the vent outlet 73 either directly into the atmosphere, or to the atmosphere through a subsequently described retention chamber.

To divert the treated mixture in the vent diverter piping 71 to the correct outlet 72 or 73, the sensor probe 74 registers the effluent perchloroethylene concentration in the vent diverter piping 71 and sends a signal that corresponds to the perchloroethylene concentration in the mixed gas that flows from the vent blower 70 to an ozone output modulation controller 75 (FIG. 1). A Payne Model 18TB-1-15 solid state variable output controller is suitable for this purpose. The ozone output modulation controller 75 is part of a microprocessor 69. A BASYS control system Model SD 1000, programmable logic controller with two each analog inputs and outputs is a microprocessor that is acceptable for this purpose. The controller 75 in the microprocessor 69 generates a variable signal to adjust the output from the power supply 58 that is applied to the ozone generator 15. By so controlling the power, the ozone output from the generator 15 is matched to meet fluctuations in the quantity of ozone needed to neutralize the perchloroethylene concentration registered by the probe 74 in the vent diverter piping 71 (FIG. 2).

An ozone output level control 76, illustratively, a manually adjustable transformer, also is a part of the microprocessor 69 (FIG. 1) and provides a safety override feature for the invention. Thus, the output level control 76 establishes a maximum setpoint level for the ozone output for the ozone generator 15. In this manner, the output level control 76 imposes a high ozone production limit on the output from the modulation controller 75 to insure that the ozone level in the diverter piping 71 does not exceed the predetermined 0.03 ppm safe concentration.

Other circuit features in the microprocessor 69 that characterize the invention include an ozone blower speed control 77 for regulating the airflow from the blower 60 to supply the inlet air throughput needed to react with perchloroethylene vapor in the dry cleaning effluent. Operation of the vent blower 70 is, in a similar manner, regulated through vent blower speed control 80. As illustrated, the vent blower speed control 80 regulates the volume of air that is discharged into the odor recirculation outlet 72 or into the odor vent outlet 73.

A switch 81 also is provided not only to energize and deenergize the apparatus 11, but also, through a 20 ampere circuit breaker that is incorporated in the switch 81, to protect the electrical circuit from damage through power surges and the like.

Figure 7:
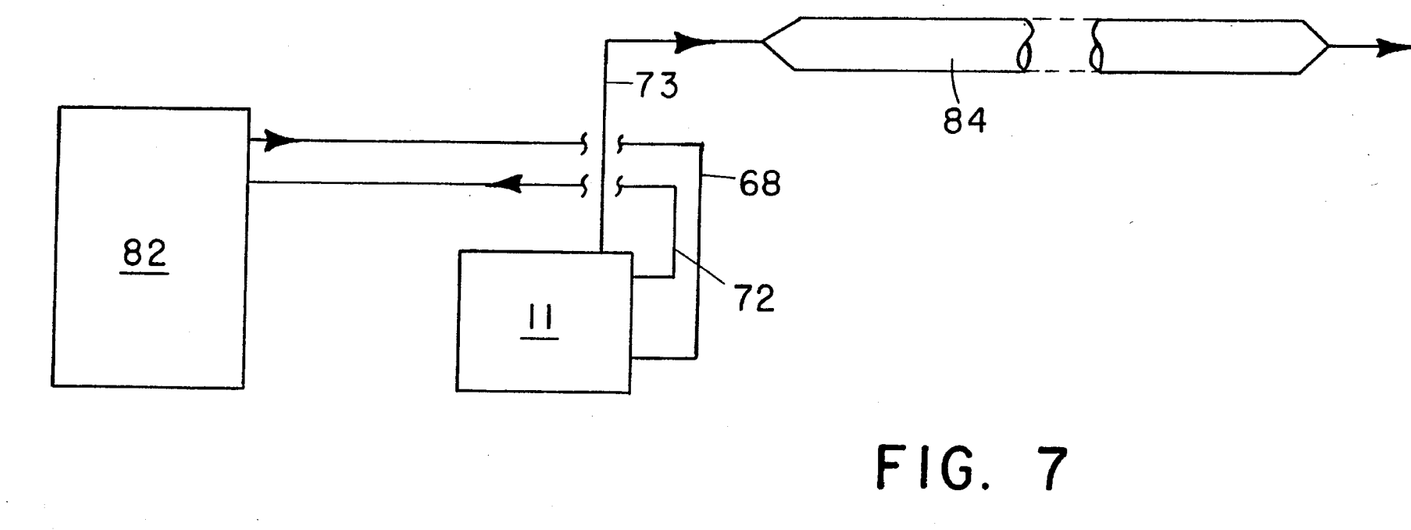
FIG. 7 is a schematic diagram for an application of the apparatus shown in FIGS. 1 through 6 to a dry cleaning process.

In operation, a dry cleaning process device 82 (FIG. 7) is activated to cleanse some clothing (not shown in the drawing). Because perchloroethylene is used as the solvent in the dry cleaning device 82, about 98% of the solvent is recovered and recycled within the device 82. The remaining 2% of the perchloroethylene escapes from the device 82 as an unrecoverable vapor.

First, the blowers 60 and 70 are energized to establish air flow through the apparatus 11 and the difference in air pressure across the ozone generator 15 is registered to make certain that there is an adequate draft of air through the ozone generator before power is applied to the two sets of electrically conductive plates within the generator. The air and vapor mixture from the dry cleaning device 82, on establishing adequate air flow then is discharged into the odor pick up inlet 68 as a saturated mixture that contains, illustratively, 1,000 ppm of perchloroethylene. The saturated mixture flows through the inlet 68 into the treatment apparatus 11, and, particularly, the mixture flows into the ozone-airborne vapor mixing compartment 67 (FIG. 4) to enable the perchloroethylene vapor to react with the ozone in order to produce the environmentally acceptable reaction products of water, carbon dioxide, oxygen (in its usual two-atom molecule) and chlorides, These reaction products, mixed with air, unreacted perchloroethylene vapor, and ozone are pumped from the mixing compartment 67 through the vent blower 70 to the vent diverter piping 71. As best shown in FIG. 2, the perchloroethylene sensor probe 74 in the diverter piping 71 responds to the perchloroethylene concentration in several ways. Thus, the exact amount of ozone required to neutralize the perchloroethylene vapor concentration is directly proportional to the amount of the vapor in the airstream entering the inlet 67. To provide a supply of ozone that is adequate, but not excessive, to react with the vapor in the airstream, a signal from the sensor probe 74 is sent to the microprocessor 69 to modulate the ozone output from the generator 15 through the ozone modulation controller 75 to match the vapor load requirement. As an additional feature of the invention, ozone output can also be set manually through the ozone output level controller 76.

The modulation controller 75 regulates the output from the high voltage power supply 58 to increase or decrease ozone production within the ozone generator 15. Thus, the ozone output from the generator is a function of several variables, all of which in accordance with the invention, are under the control of the apparatus 11. For example, by decreasing or increasing the voltage applied to the electrical conductors 21 and 46 (FIG. 6) from the high voltage power supply 58 (FIG. 3), the ozone concentration in the air that is drawn through the generator 15 is correspondingly decreased or increased. This ozone concentration and airflow combination now is also subject to control through the removal or addition of electrically conductive plates in the first set of plates 22 through 26 and second set of plates 47 and 50 through 53. A further control over ozone production is also possible through regulation of the ozone injection blower 60 (FIG. 1).

As mentioned above, however, ozone production can also be regulated through the number of plates in the first and second sets of electrically conductive plates that are mounted in the ozone generator. This additional feature of the invention provides even greater flexibility in matching ozone generation capacity through a very wide range of requirements with a single, standardized generator 15 or treatment apparatus installation.

As a consequence of this broader range of control and the ability to adjust airflow and voltage to meet ozone production needs, the volume of the apparatus 11 and the floorspace that the apparatus occupies is considerably less than that which has characterized other effluent treatment techniques. It should also be noted, in passing, that the blower 60 and the power applied to the ozone generator 15 can be controlled manually as well as automatically.

Consequently, the microprocessor 69 can respond to the perchloroethylene concentration in the vent diverter piping 71 not only by appropriately varying both the rate of air flow through the ozone generator 15 and the corona voltage that is applied to the electrical conductors 21 and 46 (FIG. 6), but also through a presetting that is determined before operation commences by selecting a number of plates in the first and second sets that correspond to a desired general range-of ozone production concentrations.

Turning once more to the sensor probe 74 that is shown in FIG. 2, a signal from this probe also regulates through a process output diverter valve 83 the flow direction for the airstream and effluents that are drawn from the mixing chamber 67 by means of the vent blower 70. Typically, an ASAHI America 2 position solenoid 120v-1-60 diverter valve is suitable for this application. In this circumstance, if the gas and vapor is to be recirculated back to the dry cleaning process device 82 (FIG. 7), the diverter valve in the vent diverter piping discharges into the recirculation outlet 72, to cause the airstream to flow back into the dry cleaning process device 82.

Should circumstances require, the diverter valve 83 can direct the airstream flow into the vent outlet 73.

If additional reaction time, moreover, is needed to treat complex hydrocarbon molecules, a secondary retention chamber 84 is provided. The secondary retention chamber 84 has a size that is determined by the dwell time required for the ozone and hydrocarbon vapor mixture to react to a degree in which the matter can be safely discharged into the atmosphere.

With respect to the illustrative case of perchloroethylene vapor treatment, the discharge from the secondary retention chamber 84 preferably should contain less than 30 ppm for atmospheric discharge.

In accordance with the invention, the secondary retention chamber 84 can be inflatable in order to accommodate the apparatus 11 and the retention chamber to the physical layout of the various industrial facilities in which the apparatus 11 is installed. For this purpose, an inflatable retention chamber of high density polyethylene (HDPE) or Teflon is suitable for the purpose of the invention. Because some reaction requirements will require a tertiary retention chamber, the provision of retention chamber lengths in multiples of 20 foot long bags is suitable for this purpose.

Manual operation of the diverter valve 83 (FIG. 2) also can be provided as an additional feature of the invention.

Turning once more to FIG. 1, it should be noted that the blower 60 draws air from the environment external to the housing 10 through the air filter 14. This airflow then passes between the individual plates in the first and second sets of plates in the ozone generator where the applied voltage corona converts some of the oxygen in the air into ozone.

Best shown in FIG. 3, the blower 60 discharges the ionized air into the automatic diverting valve 64. As mentioned above, depending on specific needs, the diverting valve 64 can direct the air and ozone mixture through the direct ozone discharge outlet 63, if for example, a volume is to be treated directly with ozone.

Recall, in this connection, that the ozone output, controller 76 can establish a safe maximum level for the output from the ozone generator 15 that will override the ozone modulation controller 75, if the modulation controller 75 increases the output from the ozone generator to a concentration that exceeds the desired safe ozone level of 0.03 ppm.

Alternatively, the automatic diverting valve 64 can be set to direct the air and ozone mixture through the ell 66 into the vapor mixing compartment 67 for perchloroethylene vapor treatment as described above.

During operation of the ozone generator 15 (FIG. 6), the glass plates 54 that are interleaved between the sets of first and second electrically conductive plates frequently become fouled, or covered with oxidation products that decrease the efficiency of the ozone generator. To reduce the time required to remove, clean and replace the glass plates in order to restore ozone generation efficiency, it is still another feature of the invention to mount the glass plates so that they are individually slidable on the electrical conductor 21. In this way, the glass plates can be removed from the ozone generated by sliding each glass plate out of the generator, thereby avoiding a cumbersome and time consuming prior art task of unbolting individual glass plates or tubes from a stainless steel frame.

An interlock 85 and an interlock timer 86 also are provided for the apparatus 11 to match the status of the treatment apparatus 11 (FIG. 7) to the operational cycle of the dry cleaning process device 82.

Thus, there is provided in accordance with the invention a safe and efficient ozone generator that can be combined with an apparatus for treating atmospheric contaminants and in particular to convert perchloroethylene vapor into environmentally acceptable substances without exposing personnel to harmful ozone concentrations.

What is claimed is:

1. Apparatus for mixing ozone with an environmental contaminant that is emitted from a source in order to neutralize the contaminant into at least one atmospherically releasable compound comprising an ozone generator for producing ozone, a blower for flowing air through said ozone generator, a mixing chamber in fluid communication with said blower for mixing ozone with an environmental contaminant to produce a mixture with an atmospherically releasable compound, means for selectively discharging said compound from said mixing chamber, a sensor for measuring the concentration of the environmental contaminant remaining in said mixture that is selectively discharged from said mixing chamber, an ozone modulation controller responsive to said sensor for increasing and decreasing ozone produced by said ozone generator in response to said sensor measurement of the environmental contaminant concentration in said mixture, a retention chamber in selective fluid communication with said mixing chamber to enable ozone to neutralize a contaminant wherein said retention chamber has an elastic structure that expands and contracts in response to said flowing air.

2. Apparatus for mixing ozone with an environmental contaminant that is emitted from a source in order to neutralize the contaminant into at least one atmospherically releasable compound comprising an ozone generator for producing ozone, a blower for flowing air through said ozone generator, a mixing chamber in fluid communication with said blower for mixing ozone with an environmental contaminant to produce a mixture with an atmospherically releasable compound, means for selectively discharging said compound from said mixing chamber, a sensor for measuring the concentration of the environmental contaminant remaining in said mixture that is selectively discharged from said mixing chamber, an ozone modulation controller responsive to said sensor for increasing and decreasing ozone produced by said ozone generator in response to said sensor measurement of the environmental contaminant concentration in said mixture wherein said ozone generator further comprises a pair of electrical conductors spaced from each other, at least two sets of electrically conductive plates, each of said sets of electrically conductive plates being coupled to a respective one of said associated electrical conductors, said sets of electrically conducting plates protruding into the space formed between said electrical conductors, said sets of electrically conductive plates being spaced from each other, said respective sets of electrically conductive plates being interleaved to establish lateral spacing between adjacent plates in each of said sets of plates and to overlap each other through a portion of their respective lengths, and glass plates nested between each adjacent pair of said electrically conductive plates.

3. An ozone generator comprising a pair of electrical conductors spaced from each other, at least two sets of electrically conductive plates, each of said sets of electrically conductive plates extending from a respective one of said associated electrical conductors into the space formed therebetween, said respective sets of electrical conductors being interleaved to establish lateral spacing between adjacent plates in each of said sets of plates and to overlap each other through a portion of their respective lengths, and glass plates nested between each adjacent pair of said electrically conductive plates.

4. An ozone generator according to claim 3, wherein said electrically conductive plates further comprise dimples formed in each of said plates, said dimples bearing against said adjacent glass plate surfaces.

5. An ozone generator according to claim 3, further comprising a stabilizer for said overlapping portions of said sets of plates, said stabilizer having dimples formed therein to bear against the adjacent glass plate surface.

6. An ozone generator according to claim 3, wherein said glass plates further comprise lengths thereof that extend the entire distance between said spaced electrical conductors, each of said glass plates being slidably removable from said respective nested positions between said sets of electrically conductive plates.

* * * * *